United States Patent [19]

Anderson

[11] Plant 3,991

[45] Dec. 14, 1976

[54] PLUM TREE

[75] Inventor: Frederic W. Anderson, Merced, Calif.

[73] Assignee: The Burchell Nursery, Inc., Modesto, Calif.

[21] Appl. No.: 656,609

[22] Filed: Feb. 9, 1976

[51] Int. Cl.[2] ..... A01H 5/00

[52] U.S. Cl. ..... Plt./38

[58] Field of Search ..... Plt./38

*Primary Examiner*—Robert E. Bagwill

*Attorney, Agent, or Firm*—Roger B. Webster

[57] ABSTRACT

A plum tree of medium size, upright to spreading, open, foliated with medium size, obovate, medium thick, medium green leaves having a coarsely serrate margin, and alternate, reniform glands positioned on the base of the blade, and a regular and productive bearer of large to medium size, globose, freestone to semi-freestone fruit having deep blue skin with a silvery-grey bloom, and yellow-green, firm to medium texture, crisp, meaty, melting flesh high in sugar content.

1 Drawing Figure

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of plum tree resulted from my endeavors in the conduct of such plant breeding program.

ORIGIN OF THE VARIETY

The present variety of plum tree was originated by me, in my experimental orchard located as aforesaid, as a $F_1$ cross of the President plum (unpatented) and the Agen (French) prune (unpatented). A large number of seedlings of the above cross were grown under conditions of careful and continuing observation by me, and—in maturity—one of such seedlings evidenced characteristics which appeared desirable for commercial production. I, therefore, selected such one seedling—and which is the present variety—for asexual reproduction and with a view toward ultimate commercial introduction of such variety.

ASEXUAL REPRODUCTION OF THE VARIETY

Subsequent to its origination and selection as above, I asexually reproduced the variety in said experimental orchard by top-working on mature orchard trees, and such reproduction ran true, in all respects, to the original seedling tree.

SUMMARY OF THE VARIETY

The present variety of plum tree is of medium size, upright to spreading, open, foliated with medium size, obovate, medium thick, medium green leaves having a coarsely serrate margin, and alternate, reniform glands positioned on the base of the blade, and a regular and productive bearer of large to medium size, globose, freestone to semi-freestone fruit having deep blue skin with a silvery-grey bloom, and yellow-green, firm to medium texture, crisp, meaty, melting flesh high in sugar content.

Further, the present variety of plum tree bears fruit (excellent for prune production) which is of the French—such as Agen—type, but, in comparison, the fruit is larger, less susceptible to growth cracks and rot, and is of a deep blue exterior color.

Additionally, the present variety of plum tree bears fruit which, in comparison to the President, is smaller and not quite as firm, but—with the same good shipping quality—is of better keeping and eating quality.

It will thus be recognized that the present variety of plum tree produces fruit having the desired characteristics for shipping and drying (or other processing), as well as for table or dessert use, fresh or cooked; all without the necessity—because of the high sugar content of the flesh—of the use of any supplemental sweetening agent.

BRIEF DESCRIPTION OF THE DRAWING

The drawing is a photographic illustration of a twig with leaves, and separate fruit; one of the latter being half cut away to expose the flesh and stone.

DESCRIPTION OF THE VARIETY

The botanical details of this new and distinct variety of plum tree—with color definitions (except those in common color terms) referenced to Maerz and Paul Dictionary of Color—are as follows:

TREE

Size: Medium.
Vigor: Vigorous.
Growth: Upright to spreading.
Density: Open.
Production: Productive.
Bearing: Regular bearer.

TRUNK

Size: Medium.
Texture: Medium.

BRANCHES

Size: Medium.
Texture: Medium.
Lenticels:
*Number.*—Few.
*Size.*—Small.

LEAVES

Size:
*Medium.*
*Average length.*—3½".
*Average width.*—2".
Form: Obovate.
Thickness: Medium.
Margin: Coarsely serrate.
Petiole:
*Medium length.*
*Medium thickness.*
Glands:
*Alternate.*
*Small.*
*Reniform.*
*Positioned on base of blade.*
Color:
*Top Side.*—Medium green (23-j-9).
*Under Side.*—Lighter green (22-L-7).

FLOWERS

Blooming Period:
*About with Agen (French) prune.*
*Medium, as compared with other varieties.*
Date of First Bloom: Mar. 20, 1975.
Date of Full Bloom: Apr. 10, 1975.

FRUIT

Maturity When Described: Eating ripe.—Oct. 15, 1975.
Date of First Picking: Sept. 10, 1975.
Date of Last Picking: Oct. 15, 1975.
Size:
*Variable.*
*Large to medium.*
*Average diameter axially.*—2⅛".
*Average transversely in suture plane.*—1½".
Form:
*Variable.*
*Globose.*
*Compressed laterally.*
Suture:
*An inconspicuous line.*
*Without depression beyond pistil point.*
Ventral Surface: Rounded slightly.
Cavity: Circular, without markings.
Apex: Very short to none.
Pistil Point: Wanting.

SKIN

Thickness: Thick to medium.
Texture: Tough to medium.
Tendency to Crack: None noted in wet or dry season.
Down: Wanting.
Color:
*Deep blue (40-L-12) shading darker toward black.*
*Bloom.*—silver-grey (39-E-5).

FLESH

Amygdalin: Wanting.
Texture:
*Firm to medium.*
*Crisp.*
*Meaty.*
*Melting.*
Fibers:
*Few.*
*Tender.*
Ripens: Evenly.
Flavor:
*Subacid.*
*Delicate.*
*Vinous.*
Aroma: Wanting.
Eating Quality: Best.
Sugar Content: Very high.
Color: Yellow green (14-K-4).

STONE

Type:
*Free to semi-free.*
*Adheres to flesh along ventral edge over upper half of sides.*
Size:
*Medium.*
*Average length.*—1".
*Average breadth.*—⅝".
*Average thickness.*—⅜".
Form: Oblong.
Base: Oblique.
Apex: Rounded.
Sides: Equal.
Surface:
*Irregularly furrowed near base.*
*Ridged near base.*
Ridges: Rounded.
Ventral Edge: Thick.
Dorsal Edge: Narrow, with shallow, narrow groove.
Tendency to Split: None.
Color: Beige (14-K-9).

USE

Market—local.
Dessert.
Culinary.
Canning.
Drying.

No supplementary sweetening agent required for any use.

KEEPING QUALITY

Excellent.

RESISTANCE TO INSECTS AND DISEASES

No unusual susceptibilities noted.
High resistance to brown rot (Monilia).

SHIPPING QUALITY

Good.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, characterized by the bearing of fruit, of best eating quality, which is very high in sugar content whereby, for any use, no supplementary sweetening agent is required.

* * * * *

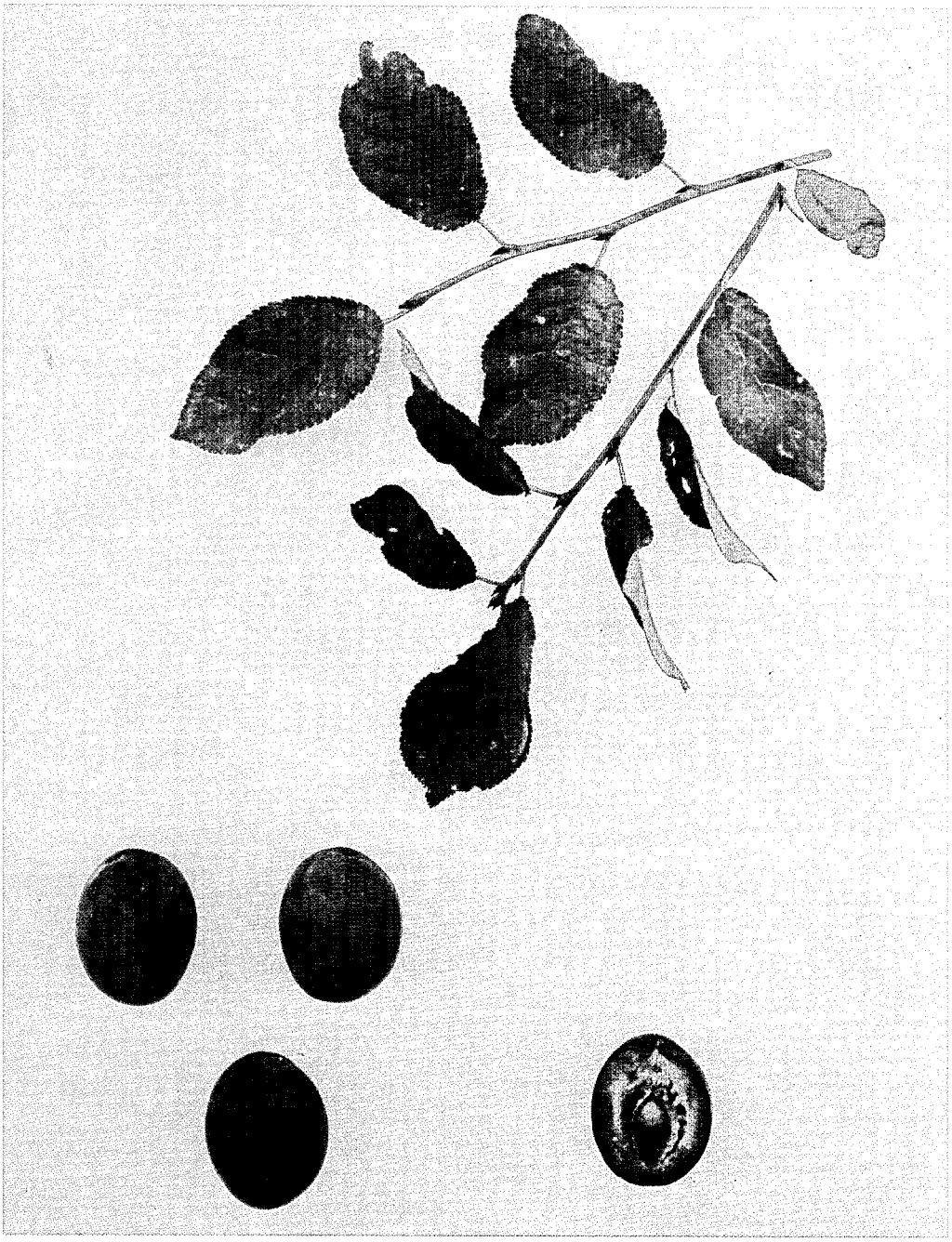

Dec. 14, 1976 F. W. ANDERSON Plant Pat. 3,991
PLUM TREE
Filed Feb. 9, 1976